United States Patent
Khattar et al.

(10) Patent No.: US 9,968,608 B2
(45) Date of Patent: May 15, 2018

(54) PHARMACEUTICAL COMPOSITIONS COMPRISING PEMETREXED AND TROMETHAMINE

(71) Applicant: Fresenius Kabi Oncology Limited, New Dehli (IN)

(72) Inventors: Dhiraj Khattar, Gurgaon (IN); Rajesh Khanna, Gurgaon (IN); Mukti Yadav, Gurgaon (IN); Krishanu Burman, Gurgaon (IN)

(73) Assignee: Fresenius Kabi Oncology Limited, New Delhi (IN)

( * ) Notice: Subject to any disclaimer, the term of this patent is extended or adjusted under 35 U.S.C. 154(b) by 0 days. days.

(21) Appl. No.: 15/200,433

(22) Filed: Jul. 1, 2016

(65) Prior Publication Data

US 2016/0310495 A1 Oct. 27, 2016

Related U.S. Application Data

(62) Division of application No. 14/403,310, filed as application No. PCT/IB2013/054456 on May 30, 2013, now Pat. No. 9,421,207.

(30) Foreign Application Priority Data

May 30, 2012 (IN) .......................... 1648/DEL/2012

(51) Int. Cl.
| | |
|---|---|
| *A61K 31/519* | (2006.01) |
| *A61K 9/00* | (2006.01) |
| *A61K 47/18* | (2017.01) |
| *A61K 9/19* | (2006.01) |
| *A61K 9/08* | (2006.01) |
| *A61K 47/02* | (2006.01) |
| *A61K 47/10* | (2017.01) |
| *A61K 47/26* | (2006.01) |

(52) U.S. Cl.
CPC .......... *A61K 31/519* (2013.01); *A61K 9/0019* (2013.01); *A61K 9/08* (2013.01); *A61K 9/19* (2013.01); *A61K 47/02* (2013.01); *A61K 47/10* (2013.01); *A61K 47/18* (2013.01); *A61K 47/183* (2013.01); *A61K 47/26* (2013.01)

(58) Field of Classification Search
CPC .................................................. A61K 31/519
USPC .................................................... 514/265.1
See application file for complete search history.

(56) References Cited

U.S. PATENT DOCUMENTS

| | | |
|---|---|---|
| 5,344,932 A | 9/1994 | Taylor |
| 6,686,365 B2 | 2/2004 | Riebesehl et al. |
| 2008/0139810 A1 | 6/2008 | Busolli et al. |
| 2011/0201631 A1 | 8/2011 | Kocherlakota et al. |

FOREIGN PATENT DOCUMENTS

| | | |
|---|---|---|
| CN | 101081301 | 12/2007 |
| CN | 100364993 | 1/2008 |
| WO | 2012/015810 | 2/2012 |

OTHER PUBLICATIONS

Jordan, V. C. Nature Reviews: Drug Discovery, 2, 2003, 205.*
Hackam, et al. JAMA, 296(14), 2006, 1731-1732.*
Hazarika et al. "Pemetrexed in Malignant Pleural Mesothelioma," Clinical Cancer Research, vol. 11, 982-992, Feb. 1, 2005.
Cohen et al., "FDA Drug Approval Summary: Premetrexed for Injection (Alimta®) for the Treatment of Non-Small Cell Lung Cancer," The Oncologist, 2005; 10:363-368.

* cited by examiner

*Primary Examiner* — Douglas M Willis
(74) *Attorney, Agent, or Firm* — Occhiuti & Rohlicek LLP

(57) ABSTRACT

A pharmaceutical composition of Pemetrexed represented by formula (I), which is a liquid ready to use solution formulation or a lyophilized pharmaceutical composition for parenteral administration comprising a pharmaceutically acceptable organic amine, an inert gas and optionally containing at least one or more pharmaceutically acceptable excipients. Also provided are processes for preparation of the ready to use solution formulation or lyophilized pharmaceutical composition of the present invention.

(I)

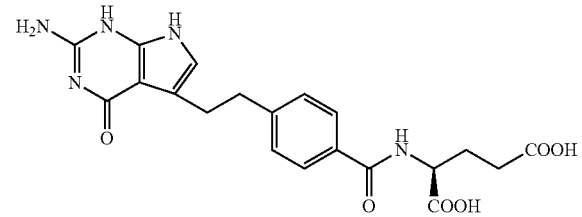

23 Claims, No Drawings

PHARMACEUTICAL COMPOSITIONS COMPRISING PEMETREXED AND TROMETHAMINE

CROSS REFERENCE TO RELATED APPLICATIONS

This application is a divisional application of U.S. application Ser. No. 14/403,310, filed Nov. 24, 2014, which is a U.S. national phase application under 35 U.S.C § 371 of International Application No. PCT/IB2013/054456, filed May 30, 2013, which claims the benefit of the filing date of Indian Application No. 1648/DEL/2012, filed May 30, 2012. The contents of the aforementioned applications are incorporated herein by reference in their entirety.

FIELD OF THE INVENTION

The present invention relates to pharmaceutical compositions of Pemetrexed containing a pharmaceutically acceptable organic amine and an inert gas. The pharmaceutical composition may optionally include other pharmaceutically acceptable excipients which comprises any one or combination of antioxidants/chelating agents/amino acids/stabilizers/preservatives/bulking agents/buffers/organic solvents/carriers/diluents/and solubilizers. The pharmaceutical compositions of the present invention are stable and pharmaceutically acceptable.

BACKGROUND OF THE INVENTION

Certain folic acid antimetabolites are known to be antineoplastic agents. These compounds inhibit enzymatic conversion involving metabolic derivatives of folic acid. One such compound described by U.S. Pat. No. 5,344,932, known as "Pemetrexed" represented by Formula-I shown below, is currently formulated into a concentrated liquid for administration as an infusion dosage form. This member of the folic acid family has been approved for treatment of malignant pleural mesothelioma and for second-line treatment of non small cell lung cancer. Pemetrexed disodium salt heptahydrate represented by Formula-II is marketed by Eli Lilly and Company under the trade name ALIMTA® as a sterile lyophilized powder for intravenous administration. The commercial product is reported to be a lyophilized powder of heptahydrate Pemetrexed disodium and mannitol. The lyophilized product is available in strengths of 100 mg/vial and 500 mg/vial and is reconstituted with 0.9% sodium chloride at a concentration of 25 mg/mL before its administration.

Formula I

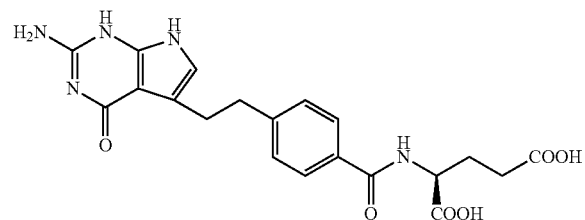

Formula II

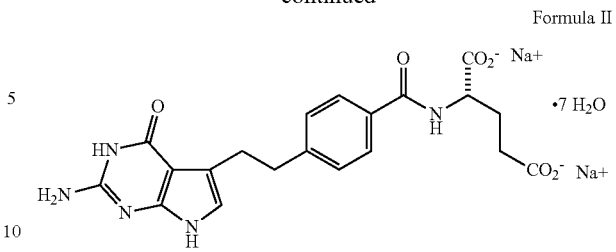

The formulation teachings of the U.S. Pat. No. 5,344,932 provides that the compounds claimed therein can be administered parenterally.

It was found that a simple, isotonic saline solution of Pemetrexed is not pharmaceutically acceptable for commercial purposes due to degradation of the solution to form unacceptable related substances. The chemical instability of Pemetrexed is mainly attributed to their oxidative and acidic degradation.

Bernd et al in U.S. Pat. No. 6,686,365 discloses a stable ready to use (RTU) formulation of Pemetrexed which is developed by using antioxidants/amino acids like L-Cysteine, Monothioglycerol and Thioglycolic acid. The preferred salt of the Pemetrexed is clearly mentioned as Pemetrexed disodium and also at least one antioxidant. The formulation disclosed is aqueous one.

Yanling et al in CN Patent No. 101081301, again discloses a RTU formulation of Pemetrexed stabilized by using antioxidant like L-arginine, L-glutathione, L-methionine and L-tryptophan. The preferred salt of the Pemetrexed is clearly mentioned as Pemetrexed disodium and also mentioned is at least one antioxidant Palepu et al in PCT Application No. WO2012/015810, claims a RTU solution formulation of Pemetrexed along with an antioxidant, a chelating agent and dissolved in a pharmaceutically acceptable fluid. The Preferred salt is Pemetrexed disodium and the composition mentioned is aqueous composition with chelating agent and antioxidant.

Chandrasekhar et al in US Patent Application Publication No. 20110201631, discloses lyophilized formulations of amorphous Pemetrexed and its salts and the preferred one is disodium salt of Pemetrexed. The amorphous form of Pemetrexed is particularly referred in this patent application.

It is indicated from all the above mentioned prior arts that all the pharmaceutical compositions of Pemetrexed utilizes the preferred salt of Pemetrexed which is Pemetrexed disodium. Antioxidants are also used in the prior art compositions. Further all the abovementioned prior art compositions are aqueous based formulations.

Further there is a prior art disclosure US 20080139810 that discloses a process for preparing disodium salt of Pemetrexed, wherein the starting material is Pemetrexed of formula I. The Pemetrexed thus utilized is converted to Pemetrexed disodium of formula II during lyophilization process. Hence, there is in-situ formation of Pemetrexed disodium during lyophilization and the final product contains Pemetrexed disodium.

In light of the abovementioned prior arts there remains a need to develop stable parenteral pharmaceutical compositions of Pemetrexed of formula I. In the present invention it was surprisingly found that Pemetrexed according to formula I containing pharmaceutically acceptable organic amines and an inert gas are favorable in formulating pharmaceutical composition for medical use.

Further controlled oxygen content with inert gas purging and/or using antioxidants/chelating agents/amino acids and maintaining higher pH values using pharmaceutically acceptable organic amines is useful in controlling the oxidative and acidic degradation of Pemetrexed respectively.

The formulation of the present invention provides the composition of Pemetrexed with pharmaceutically acceptable organic amine which is free of sodium ions of disodium salt of Pemetrexed released during the dilution of the pharmaceutical composition of Pemetrexed disodium and uses pharmaceutically acceptable organic amines to control the acidic degradation.

Against this backdrop of oxidative and acidic degradation the inventors of the present Application have surprisingly found that stable pharmaceutical compositions of Pemetrexed may be developed by utilizing Pemetrexed along with a pharmaceutically acceptable organic amine and may optionally contain some other pharmaceutically acceptable excipients.

OBJECT OF THE INVENTION

It is an object of the present invention to overcome the drawbacks of the prior art.

It is another object of the present invention to provide a stable pharmaceutical composition of Pemetrexed by utilizing Pemetrexed.

SUMMARY OF THE INVENTION

According to one aspect of the present invention there is provided a pharmaceutical composition of Pemetrexed represented by formula I,

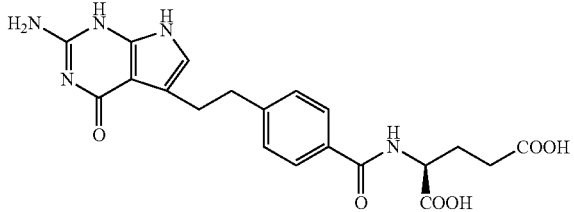 [SMILES: Nc1nc(=O)c2c(CCc3ccc(C(=O)N[C@@H](CCC(=O)O)C(=O)O)cc3)c[nH]c2[nH]1]

which is a ready to use solution composition or a lyophilized pharmaceutical composition for parenteral administration comprising a pharmaceutically acceptable organic amine, an inert gas and optionally containing at least one or more pharmaceutically acceptable excipients.

According to another aspect of the present invention there is provided a process for preparing ready to use pharmaceutical composition comprising the steps:
 a. taking suitable quantity of water for injection in vessel and adding required quantity of organic amine to the water for injection,
 b. adding organic solvent to the above mixture and mixing uniformly,
 c. purging inert gas into the solution to minimize the dissolved oxygen content,
 d. adding Pemetrexed to the above mixture and dissolving and adjusting the pH to about 6-8,
 e. filtering the solution and filling in vials,
 f. blanketing vial headspace with inert gas to achieve headspace oxygen content less than 2% and more preferably less than 0.5%,
 g. stoppering and sealing the vials.

According to yet another aspect of the present invention there is provided a process for preparing lyophilized pharmaceutical composition comprising the steps:
 a. taking suitable quantity of water for injection in vessel,
 b. purging inert gas into the water for injection to minimize the dissolved oxygen content,
 c. adding required quantity of organic amine and bulking agent and dissolving in water for injection,
 d. adding Pemetrexed and dissolving and adjusting the pH to about 6-8,
 e. making up the volume using water for injection,
 f. filtering the solution and filling in vials,
 g. stoppering the vials and lyophilizing by breaking the vacuum using inert gas.

DETAILED DESCRIPTION OF THE INVENTION

One aspect of the present invention is the preparation of the pharmaceutical composition of Pemetrexed in combination with a pharmaceutically acceptable organic amine and an inert gas which is stable.

The term "pharmaceutical composition" in accordance with the present invention refers to various dosage forms like ready to use and lyophilized pharmaceutical compositions suitable for administration of a drug, such as parenteral, intravenous, intraarterial, intramuscular, subcutaneous etc.

An organic amine is an organic compound which acts as a base. They usually contain nitrogen atoms, which can easily be protonated. The preferred organic amines of the present invention are selected from Tris(hydroxymethyl)aminomethane, N-(2-Acetamido)-2-aminoethanesulfonic acid, N-(2-(Acetamido)imino)diacetic acid, 2-Amino-2-methyl-1-propanol, 2-Amino-2-methyl-1,3-propanediol, N-(1,1-Dimethyl-2-hydroxyethyl)-3-amino-2-hydroxypropanesulfonic acid, N,N-Bis(2-hydroxyethyl)-2-aminoethanesulfonic acid, N,N-Bis(2-hydroxyethyl)glycine, 2,2'-(Propane-1,3-diyldiimino)bis[2-(hydroxymethyl)propane-1,3-diol], 2-[Bis(2-hydroxyethyl)imino]-2-(hydroxymethyl)-1,3-propanediol, 2-Aminoethanol, (2R,3R,4R,5S)-6-Methylaminohexane-1,2,3,4,5-pentol, 2,2',2"-Nitrilotriethanol. The preferred pharmaceutically acceptable organic amines are tromethamine and meglumine. The organic amines may be present in amounts of about 40 to 90% by weight of Pemetrexed of formula I.

Another aspect of the present invention is pharmaceutical compositions of Pemetrexed that is free of the sodium ions of disodium salt of Pemetrexed.

The term "pharmaceutically acceptable" refers to an ingredient that is useful in preparing a pharmaceutical composition that is generally safe, non-toxic, and neither biologically nor otherwise undesirable, and includes those acceptable for veterinary use as well as human pharmaceutical use.

In one embodiment of the present invention the pharmaceutical composition of the present invention may optionally comprise other pharmaceutically acceptable excipients which comprises any one or combination of antioxidants/chelating agents/amino acids/preservatives/bulking agents/buffers/organic solvents/carriers/diluents/and solubilizers.

The pharmaceutical compositions may further optionally include one or more pharmaceutically acceptable excipients. These pharmaceutically acceptable excipients may include one or more of: diluents or bulking agents such as dextrose, sucrose, mannose, mannitol and the like; antibacterial preservatives, including one or more of phenylmercuric nitrate, thiomersal, benzalkonium chloride, benzethonium chloride, phenol, cresol and chlorobutanol; chelating agents such as ethylenediamine tetraacetic acid (EDTA); buffers including one or more of acetate, citrate, tartarate, phosphate, benzoate, And bicarbonate buffers, and amino acids such as glutamic acid and histidine; tonicity contributors including one or more of hydrochloric acid, dextrose, mannitol, sorbitol, and lactose. Antioxidants include monothioglycerol, I-Cysteine, and thioglycolic acid, sodium metabisulfite, ascorbic acid, sodium EDTA, monoethanolamine gentisate, sodium formaldehyde sulfoxylate, sodium bisulfite.

The term "organic solvent" means an organic material, usually a liquid, capable of dissolving other substances.

Suitable solvents that can be used for preparing pharmaceutical compositions of Pemetrexed include water and any organic solvents from the various classes of solvents, such as, for example, alcohols, ketones, esters, ethers, halogenated hydrocarbons, aromatic hydrocarbons, nitriles, aprotic polar solvents, acidic solvents, and mixtures of any two or more thereof. Useful alcohols include, for example, methanol, ethanol, denatured spirits, n-propanol, isopropanol, n-butanol, isobutanol, t-butanol, polyhydroxy alcohols example ethylene glycol, glycerin, propylene glycol, polyethylene glycol, diethylene glycol, diglycerin, triethylene glycol, tetraethylene glycol, trimethylolpropane and the like. Useful ketones include acetone, propanone, 2-butanone, and the like. Useful halogenated hydrocarbons include, for example, dichloromethane, 1,2-dichloroethane, chloroform, carbon tetrachloride, chlorobenzene, and the like. Useful esters include, for example, ethyl acetate, n-propyl acetate, isopropyl acetate, n-butyl acetate, t-butyl acetate, and the like. Useful ethers include, for example, dimethyl ether, diethyl ether, methyl t-butyl ether, ethyl methyl ether, diisopropyl ether, tetrahydrofuran, dioxane, and the like. Useful aromatic hydrocarbons include, for example, toluene, xylene, and the like. Useful nitriles include acetonitrile, propionitrile, and the like. Useful aprotic polar solvents include N,N-dimethylformide (DMF), dimethylsulfoxide (DMSO), N,N-dimethylacetamide (DMA), and the like. Useful acidic solvents include formic acid, acetic acid, and the like. This listing is not intended to be exhaustive, and combinations of solvents that are useful can include more than one member of a class, and/or can be from different classes.

The above mentioned antioxidants/chelating agents/amino acids/preservatives/bulking agents/buffers/organic solvents/carriers/diluents/and solubilizers may be present in the compositions in pharmaceutically acceptable quantities.

The pharmaceutical compositions as developed by the Inventors of the present invention are provided as lyophilized powder and ready to use solutions that are suitable for parenteral administration after reconstitution with a suitable diluting fluid.

In one embodiment of the present invention, pharmaceutical compositions of Pemetrexed as per the present invention has a pH between about 4 and about 10, preferably between about 5 and 8 and more preferably in the range of about 6.0 and about 8.

According to another aspect of the present invention "stability" is referred to both the physical and chemical stability.

These formulations are presented as a single vial presentation having Pemetrexed concentrations in the range of 2.5 to 50 mg/ml of which the preferred concentration is 25 mg/ml. These pharmaceutical compositions are then administered via intravenous infusion to treat patients suffering from malignant pleural mesothelioma and for second-line treatment of non small cell lung cancer which is the approved indication of Pemetrexed.

In another embodiment of the present invention, so as to minimize oxidation of the sensitive material it is also desirable to remove headspace oxygen and moisture or both from the sealable vessel as quickly as possible. This may be aided by, for example, purging the sealable container with a gas which is substantially oxygen-free, or substantially moisture free, or substantially oxygen and moisture free before, during or after step, or any combination thereof. Purging can be expected to reduce the oxygen level in the sealable container to a level of from about 0.1% to about 10%, typically about 5% or lower, depending on the efficiency of flushing and how quickly the container is sealed after flushing.

The gas used for purging the sealable container may be any appropriate inert gas known to those in the art, the most commonly used gases being argon, helium or nitrogen, or mixtures thereof. However the most preferred inert gas is nitrogen.

In another embodiment of the present invention, to control the acidic degradation of the pharmaceutical composition of Pemetrexed, pharmaceutically acceptable organic amine is used which maintains the pH of the solution more than 7, thereby reducing the acidic degradation impurities. The preferred organic amines of the present invention include pharmaceutically acceptable organic amines such as tromethamine and meglumine, of which tromethamine is the most preferred organic amine.

In another embodiment of the present invention there is provided a process for preparing ready to use pharmaceutical composition where the process comprises the following steps:

a. taking suitable quantity of water for injection in vessel and adding required quantity of organic amine to the water for injection, b. adding organic solvent to the above mixture and mixing uniformly, c. purging inert gas into the solution to minimize the dissolved oxygen content, d. adding Pemetrexed to the above mixture and dissolving and adjusting the pH to about 6-8, e. filtering the solution and filling in vials, f. blanketing vial headspace with inert gas to achieve headspace oxygen content less than 2% and more preferably less than 0.5%, g. stoppering and sealing the vials.

In a further embodiment of the present invention there is provided a process for preparing lyophilized pharmaceutical composition comprising the steps:

a. taking suitable quantity of water for injection in vessel, b. purging inert gas into the water for injection to minimize the dissolved oxygen content, c. adding required quantity of organic amine and bulking agent and dissolving in water for injection, d. adding Pemetrexed and dissolving and adjusting the pH to about 6-8, e. making up the volume using water for injection, f. filtering the solution and filling in vials, g. stoppering the vials and lyophilizing by breaking the vacuum using inert gas.

In another embodiment of the present invention, there is provided a method of treating a subject suffering from malignant pleural mesothelioma comprising administration of a pharmaceutical composition comprising Pemetrexed (as represented by formula I), a pharmaceutically acceptable organic amine and optionally containing one or more pharmaceutically acceptable excipients. The pharmaceutically acceptable organic amine can be tromethamine, and the pharmaceutical composition can be a liquid ready to use solution formulation.

In another embodiment of the present invention, there is provided a method of treating a subject suffering from refractory non-small cell lung cancer comprising administration of a pharmaceutical composition comprising Pemetrexed (as represented by formula I), a pharmaceutically acceptable organic amine and optionally containing one or more pharmaceutically acceptable excipients. The pharmaceutically acceptable organic amine can be tromethamine, and the pharmaceutical composition can be a liquid ready to use solution formulation.

The invention is further illustrated by way of the following examples, which in no way should be construed as limiting the scope of the invention.

Examples

Various embodiments of the pharmaceutical compositions of Pemetrexed according to the present invention were prepared and studied for their stability and impurity profile when stored under accelerated stability conditions, which are illustrated below:

The pharmaceutical compositions of Pemetrexed were prepared using organic solvents along with ethanol and water without nitrogen purging or adjusting the pH with organic amines. The pharmaceutical compositions were held for stability and were found to be unacceptable.

Example 01

Pharmaceutical Composition of Pemetrexed with Ethanol and Water

| Sr. No. | Ingredients | Qty/mL Composition with Water | Qty/mL Composition with Ethanol |
|---|---|---|---|
| 1 | Pemetrexed | 25 mg | 25 mg |
| 2 | Dimethyl Acetamide | 0.34 mL | 0.34 mL |
| 3 | Propylene Glycol | 0.33 mL | 0.33 mL |
| 4 | Water | 0.33 mL | — |
| 5 | Ethanol | — | 0.33 mL |

The stability profile of the pharmaceutical composition of Pemetrexed with water and ethanol according to Example 01 is summarized in Table I.

TABLE I

Stability profile of the pharmaceutical composition of Pemetrexed with water and ethanol.

| Conditions | Results (Total Impurity %) Composition with water | Results (Total Impurity %) Composition with ethanol |
|---|---|---|
| Initial | 0.7 | 1.0 |
| 60° C./7 days | 9.5 | 19.5 |
| 40° C./75% RH/ 14 days | 4.3 | 3.4 |
| 25° C./60% RH/ 1 Month | 3.5 | 5.5 |

It is evident from the Example 01 and stability profile in Table I that there was an extensive oxidative and acidic degradation which was unacceptable.

Example 02

In order to control the oxidative degradation nitrogen purging was used which to some extent controlled the oxidative impurities.

Pharmaceutical Composition ('A' and 'B') of Pemetrexed

| Sr. No. | Ingredients | Qty/mL Composition 'A' | Qty/mL Composition 'B' |
|---|---|---|---|
| 1 | Pemetrexed | 25 mg | 25 mg |
| 2 | Dimethyl Acetamide | 0.28 mL | 0.16 mL |
| 3 | Propylene Glycol | 0.72 mL | 0.84 mL |
| 4 | Nitrogen* | q.s. | q.s. |

The pH of the pharmaceutical compositions 'A' and 'B' according to this example was found to be between 4-5 which lead to the extensive hydrolytic degradation which is unacceptable as per regulatory requirements. The stability profile of the pharmaceutical composition of Pemetrexed according to Example 02 is summarized in Table II.

TABLE II

Stability profile of the pharmaceutical composition of Pemetrexed according to Example 02

| Conditions | Results (Total Impurity %) Composition 'A' | Results (Total Impurity %) Composition 'B' |
|---|---|---|
| Initial | 0.44 | 0.44 |
| 60° C./7 days | 5.08 | 6.45 |
| 40° C./75% RH/ 14 days | 2.19 | 2.52 |
| 25° C./60% RH/ 1 Month | 1.15 | 1.16 |

It is evident from the above example that pharmaceutical compositions 'A' and 'B' the stability profile is not found to be acceptable but still found better than the Example 01 hence to control the acidic impurities use of organic amines was necessary in pharmaceutical composition of Pemetrexed.

In order to control oxidative as well as acidic degradation of Pemetrexed various experiments were performed which are described below only for illustrative.

Example 03

Pharmaceutical Composition of Pemetrexed:

| Sr. No. | Ingredients | Qty/mL |
|---|---|---|
| 1 | Pemetrexed | 25 mg |
| 2 | Tromethamine | 15 mg |
| 3 | Hydrochloric acid, if required | q.s. to pH 6-8 |
| 4 | Water for Injection | qs to 1 mL |
| 5 | Nitrogen | Nil |

TABLE III

Stability profile of the pharmaceutical composition of Pemetrexed according to Example 03

| Conditions | Related Substances % Total RS |
|---|---|
| Initial | 0.61 |
| 40° C./75% RH/14 days | 3.42 |
| 25° C./60% RH/1 Month | 3.07 |

From the above table it is evident that using tromethamine alone is not sufficient but nitrogen purging is required for composing a stable composition. This is evident from Example 04 where both nitrogen purging as well as tromethamine was used to minimize the degradation due to oxidative as well as acidic factors.

Example 04

Pharmaceutical Composition of Pemetrexed:

| Sr. No. | Ingredients | Qty/mL |
|---|---|---|
| 1 | Pemetrexed | 25 mg |
| 2 | Tromethamine | 15 mg |
| 3 | Hydrochloric acid, if required | q.s. to pH 6-8 |
| 4 | Water for Injection | qs to 1 mL |
| 5 | Nitrogen* | qs |

*Nitrogen is used for purging in bulk solution and blanketing in vial headspace

The pharmaceutical composition according to Example 04 is prepared by below mentioned process.

Suitable quantity of water for injection in a manufacturing vessel is taken. Nitrogen was purged into water for injection until dissolved oxygen content of water for injection comes less than 7 mg/L, preferably less than 3 mg/L. Continue to bubble nitrogen up to making up of the volume with water for injection. After nitrogen bubbling added and dissolved required quantity of tromethamine in water for injection. After addition of tromethamine Pemetrexed was added and dissolved. If required, adjusted the pH to 6-8 with the help of 10% w/v tromethamine solution or 10% v/v hydrochloric acid solution. Volume was made up to 100% with water for injection. Filtered the drug solution through a suitable 0.2µ filter. Filled the filtered solution into vials. Blanket the vial headspace with nitrogen to achieve headspace oxygen content less than 8%, preferably less than 2%. The vials were stoppered and finally sealed.

Stability profile of the pharmaceutical composition as mentioned in Example 04 has been summarized below in Table IV

TABLE-IV

Stability profile of the pharmaceutical composition as mentioned in Example 04

| Conditions | Assay (%) | pH | Related Substances % Total impurity |
|---|---|---|---|
| Initial | 103.8 | 6.9 | 0.37 |
| 60° C./7 days | 103.6 | 6.9 | 0.79 |
| 40° C./75% RH/14 days | 105.0 | 7.1 | 0.54 |
| 25° C./60% RH/1 Month | 106.9 | 7.1 | 0.46 |

As evident from the Table IV stability profile of the pharmaceutical composition of Example 04 is found to be superior as compared to the Example 01, 02 & 03.

Example 05

Pharmaceutical Composition of Pemetrexed

| Sr. No. | Ingredients | Qty/mL |
|---|---|---|
| 1 | Pemetrexed | 25 mg |
| 2 | Tromethamine | 15 mg |
| 3 | Hydrochloric acid, if required | q.s. to pH 6-8 |
| 4 | Propylene glycol | 50% v/v |
| 5 | Water for Injection | qs to 1 mL |
| 6 | Nitrogen* | qs |

*Nitrogen is used for purging in bulk solution and blanketing in vial headspace

The pharmaceutical composition according to Example 05 is prepared by below mentioned process.

Suitable quantity of water for injection is taken in a manufacturing vessel. Required quantity of tromethamine in water for injection was added and dissolved. Other solvents i.e., propylene glycol was added and mixed uniformly. Nitrogen was purged until dissolved oxygen content of solution comes less than 7 mg/L, preferably less than 3 mg/L. Continue to bubble nitrogen up to the filtration of the solution. Pemetrexed was added and dissolved. pH of the solution was adjusted if required to 6-8 with the help of 10% w/v tromethamine solution or 10% v/v hydrochloric acid solution. Volume was made up to 100% with water for injection. Filtered the drug solution through a suitable 0.2µ filter. The filtered solution was filled into vials. Blanket the vial headspace with nitrogen to achieve headspace oxygen content less than 8%, preferably less than 2%. The vials were stoppered and finally sealed.

Stability profile of the Formulation as mentioned in Example 05 has been summarized below in Table V:

TABLE V

Stability profile of the Formulation as mentioned in Example 05

| Conditions | Assay (%) | pH | Related Substances % Total impurity |
|---|---|---|---|
| Initial | 101.9 | 6.8 | 0.38 |
| 60° C./7 days | 100.9 | 6.9 | 1.08 |
| 40° C./75% RH/14 days | 102.0 | 6.8 | 0.60 |
| 25° C./60% RH/1 Month | 103.7 | 7.0 | 0.48 |

Example 06

Pharmaceutical Composition of Pemetrexed

| Sr. No. | Ingredients | Qty/mL |
|---|---|---|
| 1 | Pemetrexed | 25 mg |
| 2 | Tromethamine | 15 mg |
| 3 | Hydrochloric acid, if required | q.s. to pH 6-8 |
| 4 | Dimethyl acetamide | 16% v/v |
| 5 | Propylene glycol | 42% v/v |
| 6 | Water for Injection | qs to 1 mL |
| 7 | Nitrogen* | qs |

*Nitrogen is used for purging in bulk solution and blanketing in vial headspace

The pharmaceutical composition according to Example 06 is prepared by below mentioned process.

Suitable quantity of water for injection is taken in a manufacturing vessel. Required quantity of tromethamine in water for injection was added and dissolved. Other solvents i.e., PG and/or DMA were added and mixed uniformly. Nitrogen was purged until dissolved oxygen content of solution comes less than 7 mg/L, preferably less than 3 mg/L. Continue to bubble nitrogen up to the filtration of the solution. Pemetrexed was added and dissolved. pH of the solution was adjusted if required to 6-8 with the help of 10% w/v tromethamine solution or 10% v/v hydrochloric acid solution. Volume was made up to 100% with water for injection. Filtered the drug solution through a suitable 0.2μ filter. The filtered solution was filled into vials. Blanket the vial headspace with nitrogen to achieve headspace oxygen content less than 8%, preferably less than 2%. The vials were stoppered and finally sealed.

Example 07

Pharmaceutical Composition of Pemetrexed

| Sr. No. | Ingredients | Qty/mL |
| --- | --- | --- |
| 1 | Pemetrexed | 25 mg |
| 2 | Tromethamine | 15 mg |
| 3 | Hydrochloric acid, if required | q.s. to pH 6-8 |
| 4 | Dimethyl acetamide | 16% v/v |
| 5 | Propylene glycol | 42% v/v |
| 6 | Ethanol | qs to 1 mL |
| 7 | Nitrogen* | qs |

*Nitrogen is used for purging in bulk solution and blanketing in vial headspace

The pharmaceutical composition according to Example 07 is prepared by below mentioned process.

Suitable quantity of Ethanol is taken in a manufacturing vessel. Required quantity of tromethamine in Ethanol was added and dissolved. Other solvents i.e., Propylene glycol and/or Dimethylacetamide were added and mixed uniformly. Nitrogen was purged until dissolved oxygen content of solution comes less than 7 mg/L, preferably less than 3 mg/L. Continue to bubble nitrogen up to the filtration of the solution. Pemetrexed was added and dissolved. pH of the solution was adjusted if required to 6-8 with the help of 10% w/v tromethamine solution or 10% v/v hydrochloric acid solution. Volume was made up to 100% with ethanol. Filtered the drug solution through a suitable 0.2μ filter. The filtered solution was filled into vials. Blanket the vial headspace with nitrogen to achieve headspace oxygen content less than 8%, preferably less than 2%. The vials were stoppered and finally sealed.

Example 08

Pharmaceutical Composition of Pemetrexed

| Sr. No. | Ingredients | Qty/mL |
| --- | --- | --- |
| 1 | Pemetrexed | 25 mg |
| 2 | Tromethamine | 15 mg |
| 3 | Hydrochloric acid, if required | q.s. to pH 6-8 |
| 4 | Dimethyl acetamide | 33% v/v |
| 5 | Propylene glycol | 60% v/v |
| 6 | Ethanol | qs to 1 mL |
| 7 | Nitrogen* | qs |

*Nitrogen is used for purging in bulk solution and blanketing in vial headspace

The pharmaceutical composition according to Example 08 is prepared by below mentioned process.

Suitable quantity of Ethanol is taken in a manufacturing vessel. Required quantity of tromethamine in Ethanol was added and dissolved. Other solvents i.e., Propylene glycol and/or Dimethylacetamide were added and mixed uniformly. Nitrogen was purged until dissolved oxygen content of solution comes less than 7 mg/L, preferably less than 3 mg/L. Continue to bubble nitrogen up to the filtration of the solution. Pemetrexed was added and dissolved. pH of the solution was adjusted if required to 6-8 with the help of 10% w/v tromethamine solution or 10% v/v hydrochloric acid solution. Volume was made up to 100% with ethanol. Filtered the drug solution through a suitable 0.2μ filter. The filtered solution was filled into vials. Blanket the vial headspace with nitrogen to achieve headspace oxygen content less than 8%, preferably less than 2%. The vials were stoppered and finally sealed.

Example 09

Pharmaceutical Composition of Pemetrexed

| Sr. No. | Ingredients | Qty/mL |
| --- | --- | --- |
| 1 | Pemetrexed | 25 mg |
| 2 | Tromethamine | 15 mg |
| 3 | Hydrochloric acid, if required | q.s. to pH 6-8 |
| 4 | Dimethyl acetamide | 33% v/v |
| 5 | Propylene glycol | 60% v/v |
| 6 | Water for Injection | qs to 1 mL |
| 7 | Nitrogen* | qs |

*Nitrogen is used for purging in bulk solution and blanketing in vial headspace

The pharmaceutical composition according to Example 09 is prepared by below mentioned process.

Suitable quantity of water for injection was taken in a manufacturing vessel. Required quantity of tromethamine in water for injection was added and dissolved. Other solvents i.e., Propylene glycol and/or Dimethylacetamide were added and mixed uniformly. Nitrogen was purged until dissolved oxygen content of solution comes less than 7 mg/L, preferably less than 3 mg/L. Continue to bubble nitrogen up to the filtration of the solution. Pemetrexed was added and dissolved. pH of the solution was adjusted if required to 6-8 with the help of 10% w/v tromethamine solution or 10% v/v hydrochloric acid solution. Volume was made up to 100% with water for injection. Filtered the drug solution through a suitable 0.2μ filter. The filtered solution was filled into vials. Blanket the vial headspace with nitrogen to achieve headspace oxygen content less than 8%, preferably less than 2%. The vials were stoppered and finally sealed.

Example 10

Pharmaceutical Composition of Pemetrexed

| Sr. No. | Ingredients | Qty/mL |
| --- | --- | --- |
| 1 | Pemetrexed | 25 mg |
| 2 | Meglumine | 22 mg |
| 3 | Hydrochloric acid, if required | q.s. to pH 6-8 |
| 4 | Dimethyl acetamide | 33% v/v |
| 5 | Propylene glycol | 60% v/v |
| 6 | Water for Injection | qs to 1 mL |
| 7 | Nitrogen* | qs |

*Nitrogen is used for purging in bulk solution and blanketing in vial headspace

The pharmaceutical composition according to Example 10 is prepared by below mentioned process.

Suitable quantity of water for injection was taken in a manufacturing vessel. Required quantity of Meglumine in water for injection was added and dissolved. Other solvents i.e., Propylene glycol and/or Dimethylacetamide were added and mixed uniformly. Nitrogen was purged until dissolved oxygen content of solution comes less than 7 mg/L, preferably less than 3 mg/L. Continue to bubble nitrogen up to the filtration of the solution. Pemetrexed was added and dissolved. pH of the solution was adjusted if required to 6-8 with the help of 10% w/v meglumine solution or 10% v/v hydrochloric acid solution. Volume was made up to 100% with water for injection. Filtered the drug solution through a suitable 0.2μ filter. The filtered solution was filled into vials. Blanket the vial headspace with nitrogen to achieve headspace oxygen content less than 8%, preferably less than 2%. The vials were stoppered and finally sealed.

Various embodiments of the lyophilized pharmaceutical compositions of Pemetrexed according to the present invention were prepared and studied for their stability and impurity profile when stored under accelerated stability conditions, which are illustrated below:

Example 11

Pharmaceutical Composition of Pemetrexed

| Sr. No. | Ingredients | Qty/100 mg vial | Qty/500 mg vial |
|---|---|---|---|
| 1 | Pemetrexed | 100 mg | 500 mg |
| 2 | Tromethamine | 60 mg | 300 mg |
| 3 | Hydrochloric acid, if required | q.s. to pH 6-8 | q.s. to pH 6-8 |
| 4 | Bulking Agent | 100 mg | 500 mg |
| 5 | Water for Injection# | qs | qs |
| 6 | Nitrogen* | qs | qs |

*Nitrogen is used for purging in bulk solution and for vacuum break during lyophilization
Removed during Lyophilization The pharmaceutical composition according to Example 11 is prepared by below mentioned process.

Suitable quantity of water for injection was taken in a manufacturing vessel. Nitrogen was purged into water for injection until dissolved oxygen content of water for injection comes less than 7 mg/L, preferably less than 3 mg/L. Continue to bubble nitrogen. The required quantity of tromethamine and bulking agent is added and dissolved in water for injection of previous step. Pemetrexed was added and dissolved. If required, pH was adjusted to 6-8 with the help of 10% w/v tromethamine solution or 10% v/v hydrochloric acid solution. Volume was made up to 100% by Water for Injection. The drug solution was filtered through a suitable 0.2μ filter. The filtered solution was filled in vials. The vials were partially stoppered. The vials were then loaded in lyophilizer. Run the pre-defined lyophilization recipe. After lyophilization process is completed, partially break the vacuum with Nitrogen gas. The vials were stoppered and unloaded and finally sealed and labelled.

Example 12

Pharmaceutical Composition of Pemetrexed

| Sr. No. | Ingredients | Qty/100 mg vial | Qty/500 mg vial |
|---|---|---|---|
| 1 | Pemetrexed | 100 mg | 500 mg |
| 2 | Tromethamine | 60 mg | 300 mg |
| 3 | Hydrochloric acid, if required | q.s. to pH 6-8 | q.s. to pH 6-8 |
| 4 | Water for Injection# | qs | qs |
| 5 | Nitrogen* | qs | qs |

*Nitrogen is used for purging in bulk solution and for vacuum break during lyophilization
Removed during Lyophilization The pharmaceutical composition according to Example 12 is prepared by below mentioned process.

Suitable quantity of water for injection was taken in a manufacturing vessel. Nitrogen was purged into water for injection until dissolved oxygen content of water for injection comes less than 7 mg/L, preferably less than 3 mg/L. Continue to bubble nitrogen. The required quantity of tromethamine is added and dissolved in water for injection of previous step. Pemetrexed was added and dissolved. If required, pH was adjusted to 6-8 with the help of 10% w/v tromethamine solution or 10% v/v hydrochloric acid solution. Volume was made up to 100% by Water for Injection. The drug solution was filtered through a suitable 0.2μ filter. The filtered solution was filled in vials. The vials were partially stoppered. The vials were then loaded in lyophilizer. Run the pre-defined lyophilization recipe. After lyophilization process is completed, partially break the vacuum with Nitrogen gas. The vials were stoppered and unloaded and finally sealed and labelled.

Example 13

Pharmaceutical Composition of Pemetrexed

| Sr. No. | Ingredients | Qty/100 mg vial | Qty/500 mg vial |
|---|---|---|---|
| 1 | Pemetrexed | 100 mg | 500 mg |
| 2 | Meglumine | 88 mg | 440 mg |
| 3 | Hydrochloric acid, if required | q.s. to pH 6-8 | q.s. to pH 6-8 |
| 4 | Water for Injection# | qs | qs |
| 5 | Nitrogen* | qs | qs |

*Nitrogen is used for purging in bulk solution and for vacuum break during lyophilization
Removed during Lyophilization The pharmaceutical composition according to Example 13 is prepared by below mentioned process.

Suitable quantity of water for injection was taken in a manufacturing vessel. Nitrogen was purged into water for injection until dissolved oxygen content of water for injection comes less than 7 mg/L, preferably less than 3 mg/L. Continue to bubble nitrogen. The required quantity of meglumine is added and dissolved in water for injection of previous step. Pemetrexed was added and dissolved. If required, pH was adjusted to 6-8 with the help of 10% w/v meglumine solution or 10% v/v hydrochloric acid solution. Volume was made up to 100% by Water for Injection. The drug solution was filtered through a suitable 0.2μ filter. The filtered solution was filled in vials. The vials were partially stoppered. The vials were then loaded in lyophilizer. Run the pre-defined lyophilization recipe. After lyophilization process is completed, partially break the vacuum with Nitrogen gas. The vials were stoppered and unloaded and finally sealed and labelled.

The presently marketed composition of Pemetrexed 'Alimta' was compared with the formulation of the invention which is given below:

TABLE VI

Comparison of the stability profile of lyophilized composition of the present invention with Alimta

| Condition | Assay (%) | Related Substances % Total RS |
|---|---|---|
| Stability profile of lyophilized composition of present invention | | |
| Initial | 97.7 | 0.14 |
| 40° C./75% RH 1 Month | 104.0 | 0.26 |
| 40° C./75% RH 3 Month | 98.5 | 0.59 |
| 25° C./60% RH 6 Month | 99.6 | 0.32 |
| Stability data of Alimta | | |
| Initial | 100.97 | 0.13 |
| 40° C./75% RH 1 Month | — | 0.10 |
| 40° C./75% RH 3 Month | — | 0.16 |
| 25° C./60% RH 6 Month | — | 0.12 |

From the above experimental data it is apparent that lyophilized composition according to the current invention is having stability profile comparable to the currently available marketed composition Alimta.

According to the aspect of the present invention reconstitution stability of the formulation is also an important aspect. The composition of the present invention is to be injected into the body after reconstitution and further dilution. In order to verify the stability and suitability of the lyophilized composition of the lyophilized composition following experiments were conducted in various reconstituting fluids at different temperatures. The results were then compared with the currently marketed composition Alimta which are described in below Table:

TABLE VII

Comparison of Reconstituted injection stability of lyophilized composition of the present invention with Alimta in 0.9% Saline at 2-8° C.

| Condition | Assay (%) | Related Substances % Total RS |
|---|---|---|
| Reconstituted injection stability of lyophilized composition at 2-8° C. with 0.9% Saline solution | | |
| Initial | 101.6 | 0.26 |
| 24 Hrs | 102.6 | 0.25 |
| Reconstituted injection stability of Alimta at 2-8° C. with 0.9% Saline solution | | |
| Initial | 102.4 | 0.14 |
| 24 Hrs | 102.5 | 0.15 |

TABLE VIII

Comparison of Reconstituted injection stability of current lyophilized composition of the present invention with Alimta in 0.9% Saline 25° C.

| Condition | Related Substances % Total RS |
|---|---|
| Reconstituted injection stability of lyophilized composition of present invention at 25° C. with 0.9% Saline solution | |
| Initial | 0.26 |
| 24 Hrs | 0.29 |
| Reconstituted injection stability of Alimta at 25° C. with 0.9% Saline solution | |
| Initial | 0.14 |
| 24 Hrs | 0.22 |

From the above experimental data it is apparent that injection reconstitution stability of lyophilized composition of present invention is as good as Alimta in 0.9% saline.

The reconstituted stability of the lyophilized composition of present invention was also checked in Dextrose 5% solution and found suitable (Table VII)

TABLE IX

Reconstituted injection stability of Lyophilized composition of present invention with 5% Dextrose solution at 2-8° C. and 25° C.

| Condition | Related Substances % Total RS |
|---|---|
| Reconstituted injection stability of lyophilized composition with 5% Dextrose solution at 2-8° C. | |
| Initial | 0.24 |
| 24 hours | 0.28 |
| 48 hours | 0.31 |
| Reconstituted injection stability of lyophilized composition with 5% Dextrose solution at 25° C. | |
| Initial | 0.24 |
| 24 hours | 0.29 |
| 48 hours | 0.33 |

Further the dilution stability of the lyophilized composition of the present invention was also determined by using dextrose 5% solution with different concentration of 1 mg/mL and 9 mg/mL the results are articulated in Table VIII and Table IX.

TABLE X

Dilution Injection Stability data of Lyophilized composition of present invention at 2-8° C. and 25° C. with 5% Dextrose at 1 mg/mL concentration

| Condition | Related Substances % Total RS |
|---|---|
| Dilution Injection Stability data of present composition at 2-8° C. with 5% Dextrose at 1 mg/mL concentration | |
| Initial | 0.39 |
| 24 hours | 0.34 |
| 48 hours | 0.31 |
| Dilution Injection Stability data of present composition at 25° C. with 5% Dextrose at 1 mg/mL concentration | |
| Initial | 0.40 |
| 24 hours | 0.37 |
| 48 hours | 0.38 |

TABLE XI

Dilution Injection Stability data of lyophilized composition of present invention at 2-8° C. and 25° C. with 5% Dextrose at 9 mg/mL concentration

| Condition | Related Substances % Total RS |
|---|---|
| Dilution Injection Stability data of present composition at 2-8° C. with 5% Dextrose at 9 mg/mL concentration | |
| Initial | 0.24 |
| 24 hours | 0.26 |
| 48 hours | 0.29 |
| Dilution Injection Stability data of present composition at 25° C. with 5% Dextrose at 9 mg/mL concentration | |
| Initial | 0.27 |
| 24 hours | 0.32 |
| 48 hours | 0.39 |

From the above experiments it was found that the dilution stability of lyophilized composition is found suitable in Dextrose 5% solution at 1 mg/mL and 9 mg/mL concentrations.

The invention claimed is:

1. A pharmaceutical composition comprising pemetrexed represented by formula I,

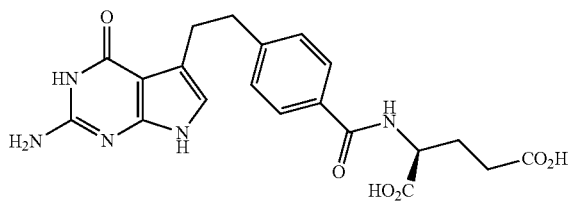

tromethamine, and water or an organic solvent, wherein the tromethamine is present in 40% to 90% by weight of the pemetrexed and the pharmaceutical composition is a liquid by virtue of inclusion of the water or the organic solvent.

2. The pharmaceutical composition of claim 1, wherein the composition further comprises a pharmaceutically acceptable excipient comprising an antioxidant, a chelating agent, an amino acid, a preservative, a bulking agent, a buffer, a carrier, a diluent or a solubilizer.

3. The pharmaceutical composition of claim 2, wherein the antioxidant is monothioglycerol, L-cysteine, thioglycolic acid, sodium metabisulfite, ascorbic acid, sodium ethylenediaminetetraacetic acid, monoethanolamine gentisate, sodium formaldehyde sulfoxylate, sodium bisulfate, or a combination thereof.

4. The pharmaceutical composition of claim 2, wherein the chelating agent is ethylenediaminetetraacetic acid.

5. The pharmaceutical composition of claim 2, wherein the amino acid is glutamic acid or histidine.

6. The pharmaceutical composition of claim 2, wherein the preservative is phenylmercuric nitrate, thiomersal, benzalkonium chloride, benzethonium chloride, phenol, cresol or chlorobutanol.

7. The pharmaceutical composition of claim 2, wherein the bulking agent is dextrose, sucrose, mannose, mannitol, or a combination thereof.

8. The pharmaceutical composition of claim 2, wherein the buffer is acetate, citrate, tartrate, phosphate, benzoate, bicarbonate, or a combination thereof.

9. The pharmaceutical composition of claim 2, wherein the organic solvent is propylene glycol, N,N-dimethylacetamide, or ethanol.

10. The pharmaceutical composition of claim 1, further comprising an inert gas.

11. The pharmaceutical composition according to claim 10, wherein the inert gas is nitrogen, helium, or argon.

12. The pharmaceutical composition of claim 11, wherein the inert gas is nitrogen.

13. The pharmaceutical composition of claim 1, wherein the pH is between 4 and 10.

14. The pharmaceutical composition of claim 13, wherein the pH is between 6 and 8.

15. The pharmaceutical composition of claim 1, wherein the composition further comprises an aqueous 5% dextrose solution or an aqueous 0.9% sodium chloride solution.

16. The pharmaceutical composition of claim 1, wherein the pemetrexed is present in an amount of is in the range of 25 mg/mL and the tromethamine is present in an amount of 15 mg/mL.

17. A method of treating a subject suffering from malignant pleural mesothelioma, the method comprising administering to a subject in need thereof the pharmaceutical composition of claim 1.

18. The method of claim 17, wherein the concentration of pemetrexed within the pharmaceutical composition is in the range of 2.5 mg/mL to 50 mg/mL.

19. A method of treating a subject suffering from refractory non-small cell lung cancer, the method comprising administering to a subject in need thereof the pharmaceutical composition of claim 1.

20. The method of claim 19, wherein the concentration of pemetrexed within the pharmaceutical composition is in the range of 2.5 mg/mL to 50 mg/mL.

21. A process for preparing the pharmaceutical composition of claim 1, the process comprising the steps of:
 (a) adding water to a vessel;
 (b) adding tromethamine to the water;
 (c) adding one or more of an additive selected from the group consisting of an organic solvent, an antioxidant and a, buffer to the mixture of step (b);
 (d) adding pemetrexed to the mixture of step (c);
 (e) adjusting the mixture of step (d) to a pH in the range of 6 to 8;
 (f) filtering the mixture of step (e) to obtain a filtrate;
 (g) collecting the filtrate obtained in step (f) in a vial; and
 (h) sealing the vial.

22. The process of claim 21, wherein step (b) further comprises purging an inert gas into the mixture.

23. The process of claim 21, wherein step (g) further comprises filling the vial headspace with an inert gas.

* * * * *